United States Patent [19]
Fontenot

[11] Patent Number: 5,549,640
[45] Date of Patent: Aug. 27, 1996

[54] DEVICE AND METHOD FOR ENHANCEMENT OF WOUND HEALING

[76] Inventor: Mark G. Fontenot, 229 Marilyn Dr., Lafayette, La. 70503-3968

[21] Appl. No.: 488,723

[22] Filed: Jun. 8, 1995

[51] Int. Cl.$^6$ ........................................ A61N 1/00
[52] U.S. Cl. ................ 607/149; 601/1; 601/18; 601/84; 601/89; 601/93; 601/103; 607/50; 607/52
[58] Field of Search ................... 601/1, 18, 84, 601/89, 93, 103; 607/50, 52, 149

[56] References Cited

U.S. PATENT DOCUMENTS

| | | | |
|---|---|---|---|
| 1,449,233 | 3/1923 | Kohn . | |
| 2,345,073 | 3/1944 | Rosett | 251/104 |
| 2,867,211 | 1/1959 | Hughes | 128/49 |
| 3,020,908 | 2/1962 | Daniels et al. | 128/6 |
| 3,352,303 | 11/1967 | Delany | 128/24 |
| 3,374,784 | 3/1968 | Brent et al. | 128/61 |
| 3,601,127 | 8/1971 | Finegold | 128/337 |
| 3,613,673 | 10/1971 | La Hue | 128/33 |
| 4,738,250 | 4/1988 | Fulkerson et al. . | |
| 4,896,680 | 1/1990 | Hirshowitz | 606/218 |
| 5,195,940 | 3/1993 | Baylink . | |
| 5,366,437 | 11/1994 | Graston . | |

FOREIGN PATENT DOCUMENTS

| | | | |
|---|---|---|---|
| 2203296 | 7/1973 | Germany | A61B 17/04 |
| 4132021 | 4/1993 | Germany . | |
| 511082 | 8/1976 | U.S.S.R. | A61H 37/00 |

*Primary Examiner*—Marvin M. Lateef
*Assistant Examiner*—Shawna J. Felger

[57] ABSTRACT

A system for application of electromechanical energy to generate full cycle linear oscillations imposing soft tissue strains which activate natural biochemical mechanisms whereby wound healing is enhanced through reduced scar tissue formation, swelling, pain, healing time, and increased wound strength is thereby provided. In essence, the device and method of this invention provides such enhanced wound healing by utilization of an applicator head which is mounted on the skin adjacent to a wound site, a cable for attachment to opposite ends of an incision's longitudinal axis which is coupled to the applicator head, a motor means for driving the cable in linear oscillations in opposite directions through alternating half cycles of a predetermined span, and an actuator means for regulating the timing and breadth of the predetermined span of each half cycle.

8 Claims, 2 Drawing Sheets

5,549,640

DEVICE AND METHOD FOR ENHANCEMENT OF WOUND HEALING

FIELD OF THE INVENTION

The present invention relates to a device and treatment for enhanced wound healing through application of an electromechanical device inducing continuous cyclic stretching and relaxation of tissue surrounding a wound site.

DESCRIPTION OF THE PRIOR ART

Each year, over 25 million surgical procedures are performed in the United States alone. Post-operative healing of tissue surrounding a wound site triggers natural biophysiologic mechanisms, including painful inflammation, immune responses and scar tissue formation.

Wounding of the soft tissue of the epidermis or dermis, whether by surgical incision or accidental imposition, triggers an inflammatory response resulting in fluid retention and turgidity, which increases the osmotic pressure of the fluid in the soft tissue surrounding the wound. The inflammatory response thus causes the soft tissue to become swollen and painful. Impairment of the healing process significantly increases risk of complications including, for example, infection, unsightly deformation of surface tissue, and chronic pain and inflammation.

Thus, a primary focus in every post-operative regime is management of the wound healing process. In wound management, healing of the incision site is monitored and treated to minimize scarring, pain and incisional swelling, healing time, and to minimize risk of healing-impairing complications.

Presently, techniques to minimize the potential risks attendant to impaired post-operative wound healing are limited. Treatments to address pain and swelling associated with inflammation include well known procedures such as application of coolant including ice or cooling packs, heat, and oral, intravenous or intramuscular administration of pharmaceutical agents such as ibuprofin, or fibroblast therapy.

Administration of conventional wound regimes also often include procedures to minimize unsightly scarring and other wound site deformation. Such procedures include mechanically effecting closure of the wound through stitching procedures and devices for interfacing the epidermal tissue surrounding the incisional site. Another treatment for unsightly scar tissue formation included in wound management regimes involves topical application of growth hormone.

Unfortunately, however, despite such conventional wound management treatments, significant risk of complications, including exacerbated and prolonged pain and swelling, as well as, infection and unsightly scar formation, due to impaired wound healing nonetheless remain. Thus, until now, no known wound management techniques have heretofore satisfactorily addressed the untoward side effects associated with wound healing.

SUMMARY OF THE INVENTION

Addressing such and other problems with devices and treatments for wound management, as further discussed below, the present invention provides a system for application of electromechanical energy to generate full cycle linear oscillations imposing soft tissue strains which activate natural biochemical mechanisms whereby wound healing is enhanced.

In essence, the device and method of this invention provides such enhanced wound healing by utilization of an applicator head which is mounted on the skin adjacent to a wound site, a cable for attachment to opposite ends of an incision's longitudinal axis which is coupled to the applicator head, a motor means for driving the cable in linear oscillations in opposite directions through alternating half cycles of a predetermined span, and an accuator means for regulating the timing and breadth of the predetermined span of each half cycle.

Each half cycle may drive the cable through a predetermined span length of up to 40% greater than the wound length, and preferably spans between about 15 percent and about 20 percent of the wound length.

The method for medical treatment of the present invention for enhancing wound healing includes providing a cable capable of being mounted across a wound site, attaching each end of the cable adjacent to opposite ends of a wound such that the cable is mounted along a line which is parallel to the longitudinal axis of the wound, and continuously driving the cable through linear oscillations of a predetermined length.

Biophysiological activity stimulated by the continuous cyclic stretching and relaxation of soft tissue along the longitudinal axis of the wound site mechanically induced by the device and method of the present invention occurs, both on an endogenous and exogenous level, underlying the enhanced healing of wounded epidermal and dermal tissue, as explained below. The movement of biopolyelectrolyte fluids and soft tissue accompanying the mechanically induced strain reduces fluid retention and turgidity and apparently enhances protein and other molecular production. Fluid movement around and through the porous, and collagenous multiphasic matrix of cells, proteins, and proteoglycan also stimulates tissue reconstruction and deposit of collagen along the wound axis. The resulting movement reduces the amount of fluid sequestered in the wound site region and causes deposit of the collagen around the wound site to be remodeled and realigned along the wound stretch axis.

Accordingly, the tissue strain imposed according to the method and device of the present invention improves primary healing by reducing retention and turgidity of fluids; remodelling the volume, length, structure, and mass of soft tissue; and aligning collagen which is reformed along the wound's longitudinal axis. Thus, enhanced wound healing, through reduced scar tissue formation, swelling, pain, healing time, and increased wound strength, is provided.

BRIEF DESCRIPTION OF THE DRAWINGS

FIG. 3 provides a diagram illustration of linear displacement associated with the present invention.

DETAILED DESCRIPTION OF THE INVENTION

Figure 1:
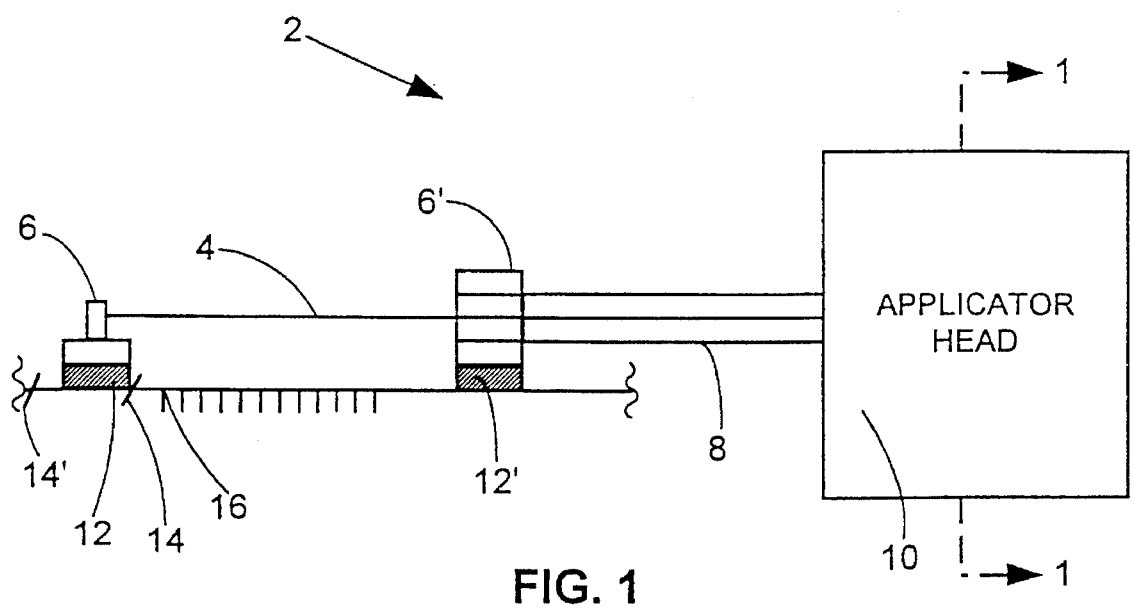
FIG. 1 is a schematic illustration of a side perspective view of a typical embodiment of the present invention.
Figure 1A:
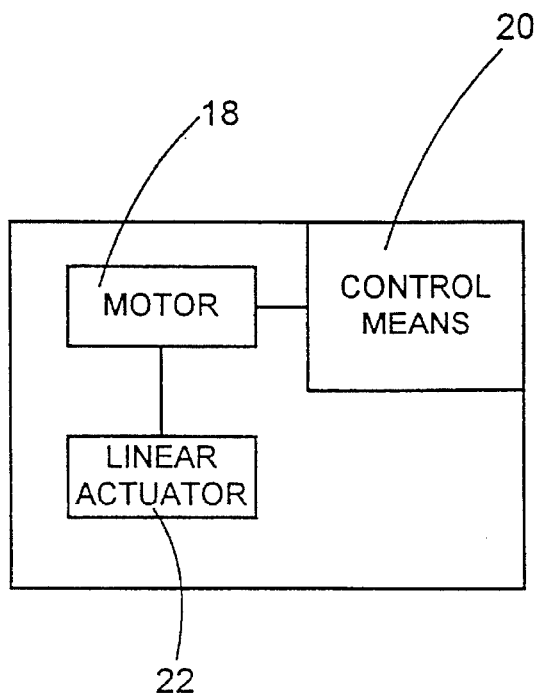
Figure 2:
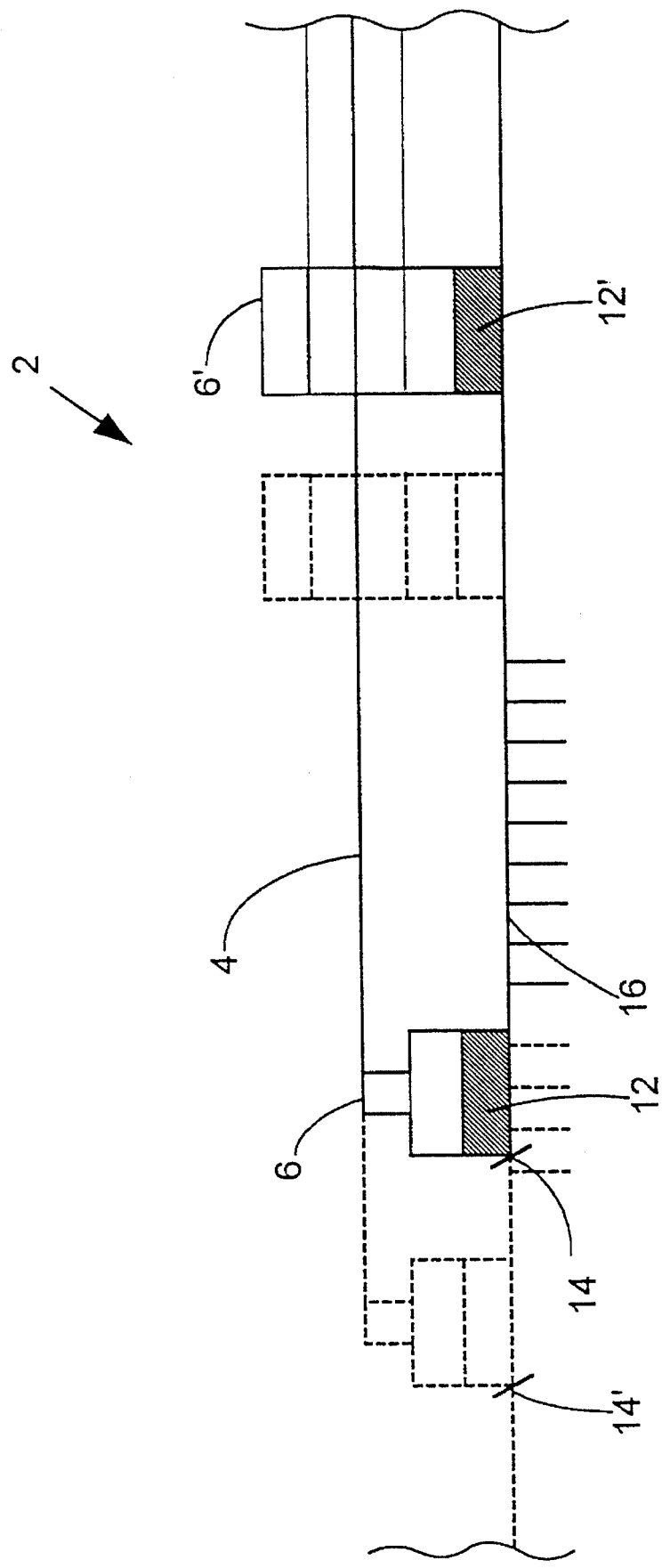
FIG. 2 provides a cross-sectional view of the device of FIG. 1 taken along line 1—1.

Referring to the drawings, FIGS. 1–1A depict an embodiment of the electromechanical device 2 of the present invention which is designed to forcibly stretch and relax an incisional wound in order to enhance wound healing. Electromechanical device 2 includes a cable 4, which may be a flexible shaft enclosed in a sleeve. Cable 4 may be coupled to poles 6 and 6' and extend to mounting fixture 8 housed within applicator head 10. Poles 6 and 6' are attached to adhesive fixtures 12 and 12', which are located at opposing ends of reference point 14, as measured when incision 16 is in a relaxed position or not subject to any force. Adhesive fixtures 12 and 12' may be adhered to the surrounding skin surface or to a surgical bandage located at opposite ends of the longitudinal axis of incision 16 with any biocompatible adhesive.

Adhesive fixtures 12 and 12' are attached to a surgical bandage adhered to poles 6 and 6' of a surgical bandage by two small pieces of adhesive material. It is particularly preferred that adhesive fixtures 12 and 12' are attached to poles 6 and 6' by corresponding hooks and loops, such as, Velcro material.

Applicator head 10 contains electric motor 18, which may be any conventional rotary stepper motor with a rack and pinion gear driving a ball bearing slide having a variable stroke length of up to 61 mm or other conventional motor. Cable 4 is coupled to the drive shaft 24 of electric motor 18. Electric motor 18 is connected to linear actuator 22 which is irreversibly coupled to cable 4. Applicator head 10 further contains control means 20. By triggering linear actuator 22, control means 20 activates the linear reciprocation of cable 4. Control means 20 is set to activate linear oscillations between two predetermined points, beginning at reference length 14, over a predetermined time of between about 5 seconds and about 180 seconds per half cycle, and average speed of about one cycle per minute. Displacement or strain effectuated by cable 4 may be between about 2 percent and about 35 percent, is typically about 5 percent to about 25 percent beyond the reference length 14 of incision 16. In the half cycle effectuating the stretch phase of the linear oscillations, the maximum force exerted by the drive shaft during the push from reference point 14 to the predetermined maximum end, i.e., stretch, to end point 14' was about 8 ounces, or 227 grams. In the half cycle effectuating the relaxed phase of the oscillation, cable 4 is returned from end point 14' to reference point 14.

Control means 20 may be a microcomputer, such as, for example, a Motorola microcomputer having 4 KB of program memory, and 2 KB of RAM data memory, and 4 8-bit I/O ports utilizing software specifically adapted for this microcomputer family. When control means 20 is regulated by computer, the time period, length, and speed or force of linear displacement is predetermined by simply entering the parameters in the keypad of the computer. In software adapted for this function, time periods between 1 and 300 seconds per second may be selected as a "RATE" parameter. The corresponding linear displacement of between one and 150 millimeters may be entered as a "SPAN" parameter. The average speed may range between about 0.00667 millimeters per second and about 300 millimeters/second. Such microcomputer control of cable 4 thus provides reliable and accurate control of the range of motion of cable 4. The "RATE," "SPAN," and start point are entered into memory of the microcomputer.

In the embodiment utilizing the Motorola microcomputer for control means 20, activation of electromechanical device of the present invention is effectuated by activation of the "RUN" command. The "RUN" command retrieves and processes through steps the stored "RATE" and "SPAN" parameters through the logic switching circuit into the drive shaft 20 for electric motor 18. When running the microcomputer controlled embodiment of the present invention, lower and upper limits activate switches which emit signals to the microprocessor immediately stepping back electrical motor 18 to return cable 4 to reference position 14.

The microcomputer records in memory data from each treatment session, including the total number of full cycle oscillations, together with the date and time of the session. A personal computer may also be programmed to set appropriate time periods, and linear displacement parameters.

EXAMPLE

A study assessing the effects of full cycle linear oscillations on wound healing in rabbits demonstrated that such collagen reformation along the longitudinal axis maximized wound strength and minimized the extent of scar tissue, resulting in overall improved wound healing.

In the study, incising in the FDP and associated articular cartilage of a test group of rabbits were subjected to continuous linear oscillations, and then compared to a control group not subjected to such treatment.

This collagen reformation indicates increased wound strength and reduced scarring. Thus, the rabbit study confirmed that cyclic linear stretching and relaxing of tissue improved primary healing and minimized scarring by inducing the polymerization of collagen in a matrix along the longitudinal stretch axis of the wound. Subsequent histologic staining of the tendon and articular tissue of the treated tissue of the test group demonstrated that collagen deposited along the stretch axis had a reduced number of cross strands linking collagen sheets and were oriented in a more vertical direction than the collagen of the control group.

It is to be understood that the present invention is not intended to be limited to the exact details of construction, operation, materials or embodiment shown and described herein, as obvious modifications and equivalent will be apparent to one skilled in the art of treating skin anomalies. For example, the device and method of the present invention could be applied to any internal strain, tear, or other injury of a ligament or muscle. This disclosure is intended to cover all alternatives, modifications and equivalents as may be included within the spirit and scope of the invention as defined by the appended claims.

The following claims represent the scope of this invention to the extent that it is subject to such delimitations. It will be appreciated by those skilled in the art that the anticipated uses and embodiments of the present invention are not amenable to precise delineation, but may vary from the exact language of the claims. Thus, the following claims are drawn not only to the explicit limitations, but also to the implicit embodiments embraced by the spirit of the claims.

What is claimed is:

1. An electromechanical device for enhancing wound healing, comprising:

a. an applicator head adapted for mounting adjacent to a site of a wound;

b. a cable coupled to the applicator head, the cable having two opposing ends and being configured to facilitate attachment of each end to skin surface surrounding opposite ends of the wound such that the cable is placed across a longitudinal axis of the wound;

c. a motor means for driving the cable in linear oscillations through alternating half cycles of a predetermined length so as to stretch and relax soft tissue surrounding the wound site; and d. means for regulating the predetermined linear displacement of the cable over each half cycle.

2. The electromechanical device of claim 1, further comprising a bandage wherein the cable is coupled to the bandage adapted for application to the wound being subject to treatment.

3. The electromechanical device of claim 1, further comprising a bandage wherein the cable is coupled to the bandage with corresponding hooks and loops.

4. The electromechanical device of claim 1, wherein the cable is adapted for attachment to the skin surface adjacent to opposite ends of the wound.

5. The electromechanical device of claim 1, wherein the predetermined length of each half cycle stretches the wound along an axis which is about 2 percent to about 35 percent greater than a length of the wound.

6. The electromechanical device of claim 1, wherein the predetermined length of each half cycle stretches the wound along an axis which is about 5 percent to about 25 percent greater than a length of the wound.

7. The electromechanical device of claim 1, wherein the means for regulating the predetermined linear displacement of the cable over each half cycle comprises a microprocessor.

8. A method for medical treatment for enhancing wound healing, comprising:
   a. providing a cable across a site of a wound, the cable having two ends;
   b. attaching each end of the cable adjacent to opposite ends of the wound such that the cable is mounted along a line which is parallel to a longitudinal axis of the wound; and
   c. using a motor to drive the cable continuously through linear oscillations of a predetermined length.

* * * * *